(12) United States Patent
Herman

(10) Patent No.: US 8,663,617 B2
(45) Date of Patent: Mar. 4, 2014

(54) WOUND HEALING PEPTIDES AND METHODS OF USE THEREOF

(71) Applicant: Tufts University, Medford, MA (US)

(72) Inventor: Ira M Herman, Newton, MA (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 13/652,889

(22) Filed: Oct. 16, 2012

(65) Prior Publication Data

US 2013/0108614 A1    May 2, 2013

Related U.S. Application Data

(62) Division of application No. 12/811,124, filed as application No. PCT/US2009/030463 on Jan. 8, 2009, now Pat. No. 8,357,655.

(60) Provisional application No. 61/010,401, filed on Jan. 8, 2008.

(51) Int. Cl.
*A61K 31/74* (2006.01)

(52) U.S. Cl.
USPC ....... 424/78.06; 514/1.1; 514/18.6; 514/21.3; 514/21.4; 514/21.5; 514/21.6; 530/300; 530/326; 530/327; 530/328

(58) Field of Classification Search
None
See application file for complete search history.

(56) References Cited

U.S. PATENT DOCUMENTS

| 5,851,522 A * | 12/1998 | Herman | 424/94.67 |
| 2005/0147679 A1 * | 7/2005 | Petito et al. | 424/484 |
| 2010/0008967 A1 * | 1/2010 | Grande et al. | 424/423 |

OTHER PUBLICATIONS

Lightfoot, Lois H. and Coolidge, Thomas B; "The distribution of collagen in the guinea pig." J. Biol. Chem. (1948) 176 p. 477-484.*
Xie, Bin et al; "Identification of the fibroblast growth factor (FGF) interacting domain in a secreted FGF binding protein by phage display." J. Biol. Chem. (2006) 281(2) p. 1137-1144.*
Lightfoot, Lois H. and Coolidge, Thomas B.; "THe distribution of collagen in the guinea pig." J. Biol. Chem. (1948) 176 p. 477-484.*
Xie, Bin et al; "Identification of the fibroblast growth factor (FGF) interacting domain in a secreted fgf-binding protein by phage display." J. Biol. Chem. (2006) 281(2) p. 1137-1144.*

* cited by examiner

*Primary Examiner* — Cecilia J Tsang
*Assistant Examiner* — Fred Reynolds
(74) *Attorney, Agent, or Firm* — Ropes & Gray LLP

(57) ABSTRACT

The current invention relates to methods and compositions for the treatment of wounds in a mammalian subject. Particularly, the invention relates to novel polypeptides and encoding nucleic acids that stimulate keratinocyte and endothelial cell motility and/or proliferation.

13 Claims, 6 Drawing Sheets

SEQUENCE LISTING

<160> NUMBER OF SEQ ID NOS: 27

<210> SEQ ID NO 1
<211> LENGTH: 13
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 1

Asp Ile Asn Glu Cys Glu Ile Gly Ala Pro Ala Gly Glu
1               5                   10

<210> SEQ ID NO 2
<211> LENGTH: 21
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 2

Asp Ile Asn Glu Cys Glu Ile Gly Ala Pro Ala Gly Glu Glu Thr Glu
1               5                   10                  15

Val Thr Val Glu Gly
            20

<210> SEQ ID NO 3
<211> LENGTH: 25
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 3

Asp Ile Asn Glu Cys Glu Ile Gly Ala Pro Ala Gly Glu Glu Thr Glu
1               5                   10                  15

Val Thr Val Glu Gly Leu Glu Pro Gly
            20                  25

<210> SEQ ID NO 4
<211> LENGTH: 14
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 4

Gly Glu Glu Thr Glu Val Thr Val Glu Gly Leu Glu Pro Gly
1               5                   10

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: Synthetic peptide -continued

```
<400> SEQUENCE: 5

Gly Val Arg Ser Cys Pro Arg Gly Cys Ser Gln Lys Gly Arg Cys Glu
1               5                   10                  15

Asp

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 6

Cys Val Cys Trp Pro Gly Tyr Thr Gly Arg Asp
1               5                   10

<210> SEQ ID NO 7
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 7

Cys Gly Thr Arg Ala Cys Pro Gly Asp Cys
1               5                   10

<210> SEQ ID NO 8
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 8

Cys Val Cys Pro Pro Gly Tyr Thr Gly Pro
1               5                   10

<210> SEQ ID NO 9
<211> LENGTH: 11
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 9

Asp Ile Asn Glu Cys Glu Leu Ser Ala Asn Leu
1               5                   10

<210> SEQ ID NO 10
<211> LENGTH: 14
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 10

Asp Ile Asp Glu Cys Glu Ser Ser Pro Cys Ile Asn Gly Val
1               5                   10
```

```
<210> SEQ ID NO 11
<211> LENGTH: 12
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 11

Met Phe Arg Lys Pro Ile Pro Ser Thr Val Lys Ala
1               5                   10

<210> SEQ ID NO 12
<211> LENGTH: 13
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 12

Ile Ile Ser Arg Cys Gln Val Cys Met Lys Met Arg Pro
1               5                   10

<210> SEQ ID NO 13
<211> LENGTH: 27
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 13

Met Phe Arg Lys Pro Ile Pro Ser Thr Val Lys Ala Pro Pro Ile Ile
1               5                   10                  15

Ser Arg Cys Gln Val Cys Met Lys Met Arg Pro
            20                  25

<210> SEQ ID NO 14
<211> LENGTH: 39
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (24)..(24)
<223> OTHER INFORMATION: a, c, g, t, unknown, or other
<220> FEATURE:
<221> NAME/KEY: modified_base
<222> LOCATION: (27)..(27)
<223> OTHER INFORMATION: a, c, g, t, unknown, or other
<220> FEATURE:
<221> NAME/KEY: modified_base
<222> LOCATION: (30)..(30)
<223> OTHER INFORMATION: a, c, g, t, unknown, or other
<220> FEATURE:
<221> NAME/KEY: modified_base
<222> LOCATION: (33)..(33)
<223> OTHER INFORMATION: a, c, g, t, unknown, or other
<220> FEATURE:
<221> NAME/KEY: modified_base
<222> LOCATION: (36)..(36)
<223> OTHER INFORMATION: a, c, g, t, unknown, or other

<400> SEQUENCE: 14
gayathaayg artgygarat hggngcnccn gcnggngar                               39
```

```
<210> SEQ ID NO 15
<211> LENGTH: 63
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (24)..(24)
<223> OTHER INFORMATION: a, c, g, t, unknown, or other
<220> FEATURE:
<221> NAME/KEY: modified_base
<222> LOCATION: (27)..(27)
<223> OTHER INFORMATION: a, c, g, t, unknown, or other
<220> FEATURE:
<221> NAME/KEY: modified_base
<222> LOCATION: (30)..(30)
<223> OTHER INFORMATION: a, c, g, t, unknown, or other
<220> FEATURE:
<221> NAME/KEY: modified_base
<222> LOCATION: (33)..(33)
<223> OTHER INFORMATION: a, c, g, t, unknown, or other
<220> FEATURE:
<221> NAME/KEY: modified_base
<222> LOCATION: (36)..(36)
<223> OTHER INFORMATION: a, c, g, t, unknown, or other
<220> FEATURE:
<221> NAME/KEY: modified_base
<222> LOCATION: (45)..(45)
<223> OTHER INFORMATION: a, c, g, t, unknown, or other
<220> FEATURE:
<221> NAME/KEY: modified_base
<222> LOCATION: (51)..(51)
<223> OTHER INFORMATION: a, c, g, t, unknown, or other
<220> FEATURE:
<221> NAME/KEY: modified_base
<222> LOCATION: (54)..(54)
<223> OTHER INFORMATION: a, c, g, t, unknown, or other
<220> FEATURE:
<221> NAME/KEY: modified_base
<222> LOCATION: (57)..(57)
<223> OTHER INFORMATION: a, c, g, t, unknown, or other
<220> FEATURE:
<221> NAME/KEY: modified_base
<222> LOCATION: (63)..(63)
<223> OTHER INFORMATION: a, c, g, t, unknown, or other

<400> SEQUENCE: 15
gayathaayg artgygarat hggngcnccn gcnggngarg aracngargt nacngtngar      60 ggn                                                                   63

<210> SEQ ID NO 16
<211> LENGTH: 75
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (24)..(24)
<223> OTHER INFORMATION: a, c, g, t, unknown, or other
<220> FEATURE:
<221> NAME/KEY: modified_base
<222> LOCATION: (27)..(27)
<223> OTHER INFORMATION: a, c, g, t, unknown, or other
<220> FEATURE:
<221> NAME/KEY: modified_base
<222> LOCATION: (30)..(30)
<223> OTHER INFORMATION: a, c, g, t, unknown, or other
<220> FEATURE:
<221> NAME/KEY: modified_base
<222> LOCATION: (33)..(33)
<223> OTHER INFORMATION: a, c, g, t, unknown, or other
```

```
<220> FEATURE:
<221> NAME/KEY: modified_base
<222> LOCATION: (36)..(36)
<223> OTHER INFORMATION: a, c, g, t, unknown, or other
<220> FEATURE:
<221> NAME/KEY: modified_base
<222> LOCATION: (45)..(45)
<223> OTHER INFORMATION: a, c, g, t, unknown, or other
<220> FEATURE:
<221> NAME/KEY: modified_base
<222> LOCATION: (51)..(51)
<223> OTHER INFORMATION: a, c, g, t, unknown, or other
<220> FEATURE:
<221> NAME/KEY: modified_base
<222> LOCATION: (54)..(54)
<223> OTHER INFORMATION: a, c, g, t, unknown, or other
<220> FEATURE:
<221> NAME/KEY: modified_base
<222> LOCATION: (57)..(57)
<223> OTHER INFORMATION: a, c, g, t, unknown, or other
<220> FEATURE:
<221> NAME/KEY: modified_base
<222> LOCATION: (63)..(63)
<223> OTHER INFORMATION: a, c, g, t, unknown, or other
<220> FEATURE:
<221> NAME/KEY: modified_base
<222> LOCATION: (66)..(66)
<223> OTHER INFORMATION: a, c, g, t, unknown, or other
<220> FEATURE:
<221> NAME/KEY: modified_base
<222> LOCATION: (72)..(72)
<223> OTHER INFORMATION: a, c, g, t, unknown, or other
<220> FEATURE:
<221> NAME/KEY: modified_base
<222> LOCATION: (75)..(75)
<223> OTHER INFORMATION: a, c, g, t, unknown, or other

<400> SEQUENCE: 16
gayathaayg artgygarat hggngcnccn gcnggngarg aracngargt nacngtngar      60
ggnmtngarc cnggn                                                      75

<210> SEQ ID NO 17
<211> LENGTH: 42
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (3)..(3)
<223> OTHER INFORMATION: a, c, g, t, unknown, or other
<220> FEATURE:
<221> NAME/KEY: modified_base
<222> LOCATION: (12)..(12)
<223> OTHER INFORMATION: a, c, g, t, unknown, or other
<220> FEATURE:
<221> NAME/KEY: modified_base
<222> LOCATION: (18)..(18)
<223> OTHER INFORMATION: a, c, g, t, unknown, or other
<220> FEATURE:
<221> NAME/KEY: modified_base
<222> LOCATION: (21)..(21)
<223> OTHER INFORMATION: a, c, g, t, unknown, or other
<220> FEATURE:
<221> NAME/KEY: modified_base
<222> LOCATION: (24)..(24)
<223> OTHER INFORMATION: a, c, g, t, unknown, or other
<220> FEATURE:
<221> NAME/KEY: modified_base
<222> LOCATION: (30)..(30)
<223> OTHER INFORMATION: a, c, g, t, unknown, or other
<220> FEATURE:
<221> NAME/KEY: modified_base
<222> LOCATION: (33)..(33)
<223> OTHER INFORMATION: a, c, g, t, unknown, or other
```

-continued

```
<220> FEATURE:
<221> NAME/KEY: modified_base
<222> LOCATION: (39)..(39)
<223> OTHER INFORMATION: a, c, g, t, unknown, or other
<220> FEATURE:
<221> NAME/KEY: modified_base
<222> LOCATION: (42)..(42)
<223> OTHER INFORMATION: a, c, g, t, unknown, or other

<400> SEQUENCE: 17
ggngargara cngargtnac ngtngarggn mtngarccng gn                    42

<210> SEQ ID NO 18
<211> LENGTH: 51
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (3)..(3)
<223> OTHER INFORMATION: a, c, g, t, unknown, or other
<220> FEATURE:
<221> NAME/KEY: modified_base
<222> LOCATION: (6)..(6)
<223> OTHER INFORMATION: a, c, g, t, unknown, or other
<220> FEATURE:
<221> NAME/KEY: modified_base
<222> LOCATION: (9)..(9)
<223> OTHER INFORMATION: a, c, g, t, unknown, or other
<220> FEATURE:
<221> NAME/KEY: modified_base
<222> LOCATION: (12)..(12)
<223> OTHER INFORMATION: a, c, g, t, unknown, or other
<220> FEATURE:
<221> NAME/KEY: modified_base
<222> LOCATION: (18)..(18)
<223> OTHER INFORMATION: a, c, g, t, unknown, or other
<220> FEATURE:
<221> NAME/KEY: modified_base
<222> LOCATION: (21)..(21)
<223> OTHER INFORMATION: a, c, g, t, unknown, or other
<220> FEATURE:
<221> NAME/KEY: modified_base
<222> LOCATION: (24)..(24)
<223> OTHER INFORMATION: a, c, g, t, unknown, or other
<220> FEATURE:
<221> NAME/KEY: modified_base
<222> LOCATION: (30)..(30)
<223> OTHER INFORMATION: a, c, g, t, unknown, or other
<220> FEATURE:
<221> NAME/KEY: modified_base
<222> LOCATION: (39)..(39)
<223> OTHER INFORMATION: a, c, g, t, unknown, or other
<220> FEATURE:
<221> NAME/KEY: modified_base
<222> LOCATION: (42)..(42)
<223> OTHER INFORMATION: a, c, g, t, unknown, or other

<400> SEQUENCE: 18
ggngtnmgnw sntgyccnmg nggntgywsn caraarggnm gntgygarga y          51

<210> SEQ ID NO 19
<211> LENGTH: 33
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (6)..(6)
<223> OTHER INFORMATION: a, c, g, t, unknown, or other
```

```
<220> FEATURE:
<221> NAME/KEY: modified_base
<222> LOCATION: (15)..(15)
<223> OTHER INFORMATION: a, c, g, t, unknown, or other
<220> FEATURE:
<221> NAME/KEY: modified_base
<222> LOCATION: (18)..(18)
<223> OTHER INFORMATION: a, c, g, t, unknown, or other
<220> FEATURE:
<221> NAME/KEY: modified_base
<222> LOCATION: (24)..(24)
<223> OTHER INFORMATION: a, c, g, t, unknown, or other
<220> FEATURE:
<221> NAME/KEY: modified_base
<222> LOCATION: (27)..(27)
<223> OTHER INFORMATION: a, c, g, t, unknown, or other
<220> FEATURE:
<221> NAME/KEY: modified_base
<222> LOCATION: (30)..(30)
<223> OTHER INFORMATION: a, c, g, t, unknown, or other

<400> SEQUENCE: 19
tgygtntgyt ggccnggnta yacnggnmgn gay                              33

<210> SEQ ID NO 20
<211> LENGTH: 30
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (6)..(6)
<223> OTHER INFORMATION: a, c, g, t, unknown, or other
<220> FEATURE:
<221> NAME/KEY: modified_base
<222> LOCATION: (9)..(9)
<223> OTHER INFORMATION: a, c, g, t, unknown, or other
<220> FEATURE:
<221> NAME/KEY: modified_base
<222> LOCATION: (12)..(12)
<223> OTHER INFORMATION: a, c, g, t, unknown, or other
<220> FEATURE:
<221> NAME/KEY: modified_base
<222> LOCATION: (15)..(15)
<223> OTHER INFORMATION: a, c, g, t, unknown, or other
<220> FEATURE:
<221> NAME/KEY: modified_base
<222> LOCATION: (21)..(21)
<223> OTHER INFORMATION: a, c, g, t, unknown, or other
<220> FEATURE:
<221> NAME/KEY: modified_base
<222> LOCATION: (24)..(24)
<223> OTHER INFORMATION: a, c, g, t, unknown, or other

<400> SEQUENCE: 20
tgyggnacnm gngcntgycc nggngaytgy                                  30

<210> SEQ ID NO 21
<211> LENGTH: 30
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (6)..(6)
<223> OTHER INFORMATION: a, c, g, t, unknown, or other
<220> FEATURE:
<221> NAME/KEY: modified_base
<222> LOCATION: (12)..(12)
<223> OTHER INFORMATION: a, c, g, t, unknown, or other
```

```
<220> FEATURE:
<221> NAME/KEY: modified_base
<222> LOCATION: (15)..(15)
<223> OTHER INFORMATION: a, c, g, t, unknown, or other
<220> FEATURE:
<221> NAME/KEY: modified_base
<222> LOCATION: (18)..(18)
<223> OTHER INFORMATION: a, c, g, t, unknown, or other
<220> FEATURE:
<221> NAME/KEY: modified_base
<222> LOCATION: (24)..(24)
<223> OTHER INFORMATION: a, c, g, t, unknown, or other
<220> FEATURE:
<221> NAME/KEY: modified_base
<222> LOCATION: (27)..(27)
<223> OTHER INFORMATION: a, c, g, t, unknown, or other
<220> FEATURE:
<221> NAME/KEY: modified_base
<222> LOCATION: (30)..(30)
<223> OTHER INFORMATION: a, c, g, t, unknown, or other

<400> SEQUENCE: 21
tgygtntgyc cnccnggnta yacnggnccn                                        30

<210> SEQ ID NO 22
<211> LENGTH: 33
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (21)..(21)
<223> OTHER INFORMATION: a, c, g, t, unknown, or other
<220> FEATURE:
<221> NAME/KEY: modified_base
<222> LOCATION: (24)..(24)
<223> OTHER INFORMATION: a, c, g, t, unknown, or other
<220> FEATURE:
<221> NAME/KEY: modified_base
<222> LOCATION: (27)..(27)
<223> OTHER INFORMATION: a, c, g, t, unknown, or other
<220> FEATURE:
<221> NAME/KEY: modified_base
<222> LOCATION: (33)..(33)
<223> OTHER INFORMATION: a, c, g, t, unknown, or other

<400> SEQUENCE: 22
gayathaayg artgygarmt nwsngcnaay mtn                                    33

<210> SEQ ID NO 23
<211> LENGTH: 42
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (21)..(21)
<223> OTHER INFORMATION: a, c, g, t, unknown, or other
<220> FEATURE:
<221> NAME/KEY: modified_base
<222> LOCATION: (24)..(24)
<223> OTHER INFORMATION: a, c, g, t, unknown, or other
<220> FEATURE:
<221> NAME/KEY: modified_base
<222> LOCATION: (27)..(27)
<223> OTHER INFORMATION: a, c, g, t, unknown, or other
<220> FEATURE:
<221> NAME/KEY: modified_base
<222> LOCATION: (39)..(39)
<223> OTHER INFORMATION: a, c, g, t, unknown, or other
```

```
<220> FEATURE:
<221> NAME/KEY: modified_base
<222> LOCATION: (42)..(42)
<223> OTHER INFORMATION: a, c, g, t, unknown, or other

<400> SEQUENCE: 23
gayathgayg artgygarws nwsnccntgy athaayggng tn                              42

<210> SEQ ID NO 24
<211> LENGTH: 36
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (9)..(9)
<223> OTHER INFORMATION: a, c, g, t, unknown, or other
<220> FEATURE:
<221> NAME/KEY: modified_base
<222> LOCATION: (15)..(15)
<223> OTHER INFORMATION: a, c, g, t, unknown, or other
<220> FEATURE:
<221> NAME/KEY: modified_base
<222> LOCATION: (21)..(21)
<223> OTHER INFORMATION: a, c, g, t, unknown, or other
<220> FEATURE:
<221> NAME/KEY: modified_base
<222> LOCATION: (24)..(24)
<223> OTHER INFORMATION: a, c, g, t, unknown, or other
<220> FEATURE:
<221> NAME/KEY: modified_base
<222> LOCATION: (27)..(27)
<223> OTHER INFORMATION: a, c, g, t, unknown, or other
<220> FEATURE:
<221> NAME/KEY: modified_base
<222> LOCATION: (30)..(30)
<223> OTHER INFORMATION: a, c, g, t, unknown, or other
<220> FEATURE:
<221> NAME/KEY: modified_base
<222> LOCATION: (36)..(36)
<223> OTHER INFORMATION: a, c, g, t, unknown, or other

<400> SEQUENCE: 24
atgttymgna arccnathcc nwsnacngtn aargcn                                    36

<210> SEQ ID NO 25
<211> LENGTH: 39
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (9)..(9)
<223> OTHER INFORMATION: a, c, g, t, unknown, or other
<220> FEATURE:
<221> NAME/KEY: modified_base
<222> LOCATION: (12)..(12)
<223> OTHER INFORMATION: a, c, g, t, unknown, or other
<220> FEATURE:
<221> NAME/KEY: modified_base
<222> LOCATION: (21)..(21)
<223> OTHER INFORMATION: a, c, g, t, unknown, or other
<220> FEATURE:
<221> NAME/KEY: modified_base
<222> LOCATION: (36)..(36)
<223> OTHER INFORMATION: a, c, g, t, unknown, or other
<220> FEATURE:
<221> NAME/KEY: modified_base
<222> LOCATION: (39)..(39)
<223> OTHER INFORMATION: a, c, g, t, unknown, or other
```

<400> SEQUENCE: 25
athathwsnm gntgycargt ntgyatgaar atgmgnccn                                    39

<210> SEQ ID NO 26
<211> LENGTH: 81
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: modified_base
<222> LOCATION: (9)..(9)
<223> OTHER INFORMATION: a, c, g, t, unknown, or other
<220> FEATURE:
<221> NAME/KEY: modified_base
<222> LOCATION: (15)..(15)
<223> OTHER INFORMATION: a, c, g, t, unknown, or other
<220> FEATURE:
<221> NAME/KEY: modified_base
<222> LOCATION: (21)..(21)
<223> OTHER INFORMATION: a, c, g, t, unknown, or other
<220> FEATURE:
<221> NAME/KEY: modified_base
<222> LOCATION: (24)..(24)
<223> OTHER INFORMATION: a, c, g, t, unknown, or other
<220> FEATURE:
<221> NAME/KEY: modified_base
<222> LOCATION: (27)..(27)
<223> OTHER INFORMATION: a, c, g, t, unknown, or other
<220> FEATURE:
<221> NAME/KEY: modified_base
<222> LOCATION: (30)..(30)
<223> OTHER INFORMATION: a, c, g, t, unknown, or other
<220> FEATURE:
<221> NAME/KEY: modified_base
<222> LOCATION: (36)..(36)
<223> OTHER INFORMATION: a, c, g, t, unknown, or other
<220> FEATURE:
<221> NAME/KEY: modified_base
<222> LOCATION: (39)..(39)
<223> OTHER INFORMATION: a, c, g, t, unknown, or other
<220> FEATURE:
<221> NAME/KEY: modified_base
<222> LOCATION: (42)..(42)
<223> OTHER INFORMATION: a, c, g, t, unknown, or other
<220> FEATURE:
<221> NAME/KEY: modified_base
<222> LOCATION: (51)..(51)
<223> OTHER INFORMATION: a, c, g, t, unknown, or other
<220> FEATURE:
<221> NAME/KEY: modified_base
<222> LOCATION: (54)..(54)
<223> OTHER INFORMATION: a, c, g, t, unknown, or other
<220> FEATURE:
<221> NAME/KEY: modified_base
<222> LOCATION: (63)..(63)
<223> OTHER INFORMATION: a, c, g, t, unknown, or other
<220> FEATURE:
<221> NAME/KEY: modified_base
<222> LOCATION: (78)..(78)
<223> OTHER INFORMATION: a, c, g, t, unknown, or other
<220> FEATURE:
<221> NAME/KEY: modified_base
<222> LOCATION: (81)..(81)
<223> OTHER INFORMATION: a, c, g, t, unknown, or other

<400> SEQUENCE: 26
atgttymgna arccnathcc nwsnacngtn aargcnccnc cnathathws nmgntgycar             60
gtntgyatga aratgmgncc n                                                      81

<210> SEQ ID NO 27
<211> LENGTH: 6
<212> TYPE: PRT
<213> ORGANISM: Artificial Sequence -continued

```
<220> FEATURE:
<221> NAME/KEY: source
<223> OTHER INFORMATION: Synthetic 6xHis tag

<400> SEQUENCE: 27

His His His His His His
1               5
```

WOUND HEALING PEPTIDES AND METHODS OF USE THEREOF

GOVERNMENT SUPPORT

The technology described here in was supported in whole or in part by Grant No. NIH EY 15125 from the National Institutes of Health. The Government has certain rights in the invention.

BACKGROUND

Wound healing and chemotactic properties of peptides obtained by collagenase-digestion of collagen have been known since the late 1970s. See, Postlethwaite et al., *Proceedings of the National Academy of Science*, 75:871-875 (1978).

Under normal circumstances, the process of acute wound healing can be broken down into three (3) phases. An initial inflammatory phase, which is followed by robust tissue remodeling and proliferation (the proliferative phase), is succeeded by a 'maturational phase' wherein re-epithelialization, dermal angiogenesis and wound closure ensues. Re-epithelialization involves the migration and proliferation of epithelial tissue, primarily keratinocytes. Angiogenesis is the growth of new blood vessels from pre-existing conduits, and is regulated by a panoply of soluble cytokines including growth factor polypeptides, as well as cell-cell and cell-matrix interactions. Chronic wounds exhibit a different healing profile from normal acute wounds in that they generally remain in an inflamed state for protracted periods of time. Non-healing wounds can most commonly be observed amongst people with diabetes, venous stasis disease, and in those patients who are immobilized. In view of the foregoing, it would be desirable to provide new biomolecules that safely and efficiently potentiate epithelial and vascular wound healing mechanisms in both acute and chronic wound healing situations.

SUMMARY OF THE INVENTION

Provided herein are methods and compositions for the promotion of wound healing. In one aspect, methods to promote wound healing in a subject in need thereof are provided. In some embodiments, one or more peptides containing one or more amino acid sequences selected from SEQ ID NOs: 1-3 are administered to a patient in need thereof. In certain embodiments, the one or more peptides are administered in an amount effective to enhance the rate of migration of keratinocytes or endothelial cells, or a combination of keratinocytes and endothelial cells, towards a wound edge. In other embodiments, the administration of the one or more peptides results in an increase in the re-epithelialization of the wound, or an increase in angiogenesis in or near the wound. In some embodiments, the administration of the one or more peptides induces re-stimulation of granulation tissue formation and the re-initiation of wound healing in tissues previously trapped in a non-healing or chronically-inflamed state. Optionally, the one or more peptides are administered at a wound site. The wound can be, e.g., a thermal, chronic, acute or surgical wound. In some embodiments, the method comprises administering to the subject a second agent. The second agent can be a compound that also promotes wound healing. In some embodiments, the second agent is a polypeptide. In some embodiments, the second agent can be, for example, a growth factor, cytokine, or enzyme.

In another aspect, the methods of promoting wound healing in a subject in need thereof comprise administering to the subject one or more peptides containing an amino acid sequence of SEQ ID NOs: 4-13.

In a third aspect isolated polypeptides are provided. In some embodiments, the isolated polypeptide contains an amino acid sequence selected from SEQ ID NOs: 1-3. In certain embodiments, one or more amino acids of the polypeptide contain a chemically modified amino acid.

In a fourth aspect isolated polypeptides containing an amino acid sequence selected from SEQ ID NOs: 4-13 are provided.

In a fifth aspect isolated nucleic acid molecule including a nucleic acid sequence of SEQ ID NOs: 14-26 are provided.

In a sixth aspect nucleic acid vectors containing a nucleic acid sequence of SEQ ID NOs: 14-26 are provided.

In a seventh aspect kits are provided. In some embodiments, the kits include, in one or more containers, one or more peptides comprising an amino acid sequence selected from SEQ ID NOs: 1-3 and instructions for administering the one or more peptides to a patient. In some embodiments, the kit includes in one or more containers, one or more peptides comprising an amino acid sequence selected from SEQ ID NOs: 1-3 and instructions for administering the one or more peptides to a patient with a bacterial collagenase. In some embodiments, the kit includes a bacterial collagenase.

In an eighth aspect the kits include, in one or more containers, one or more peptides comprising an amino acid sequence selected from SEQ ID NOs: 1-3, and a bio-compatible wound product. In some embodiments, the kit also includes a growth factor, cytokine, or enzyme.

In a ninth aspect the kits include one or more peptides comprising a sequence selected from SEQ ID NOs: 1-3 and instructions for administering the peptide in conjunction with a bio-compatible wound product.

In a tenth aspect articles of manufacture are provided. In some embodiments, the article of manufacture includes a peptide comprising an amino acid sequence selected from SEQ ID NOs: 1-3 and a growth factor, cytokine, or enzyme. In some embodiments, the article is suitable for use in a medical treatment of a mammalian subject. In some embodiments, the article of manufacture can be, for example, a skin or tissue equivalent, or a stent. The article may also contain a growth factor, cytokine, or enzyme, such as a non-human collagenase.

In an eleventh aspect absorbent product is provided. In some embodiments, the absorbent product comprises a liquid absorbent structure and one or more peptides. In some embodiment the peptide comprises an amino acid sequence selected from SEQ ID NOs: 1-3. In some embodiments, the liquid absorbent structure can be a bandage, gauze, wound or sore dressing, dermal patch, or adhesive tape.

The various embodiments described herein can be complimentary and can be combined or used together in a manner understood by the skilled person in view of the teachings contained herein. Unless otherwise defined, all technical and scientific terms used herein have the same meaning as commonly understood by one of ordinary skill in the art to which technology provided herein belongs. Although methods and materials similar or equivalent to those described herein can be used in the practice or testing of aspects of the technology provided herein, suitable methods and materials are described below. All publications, patent applications, patents, and other references mentioned herein are incorporated by reference in their entirety. In the case of conflict, the present specification, including definitions, will control. In addition,

Figure 1:
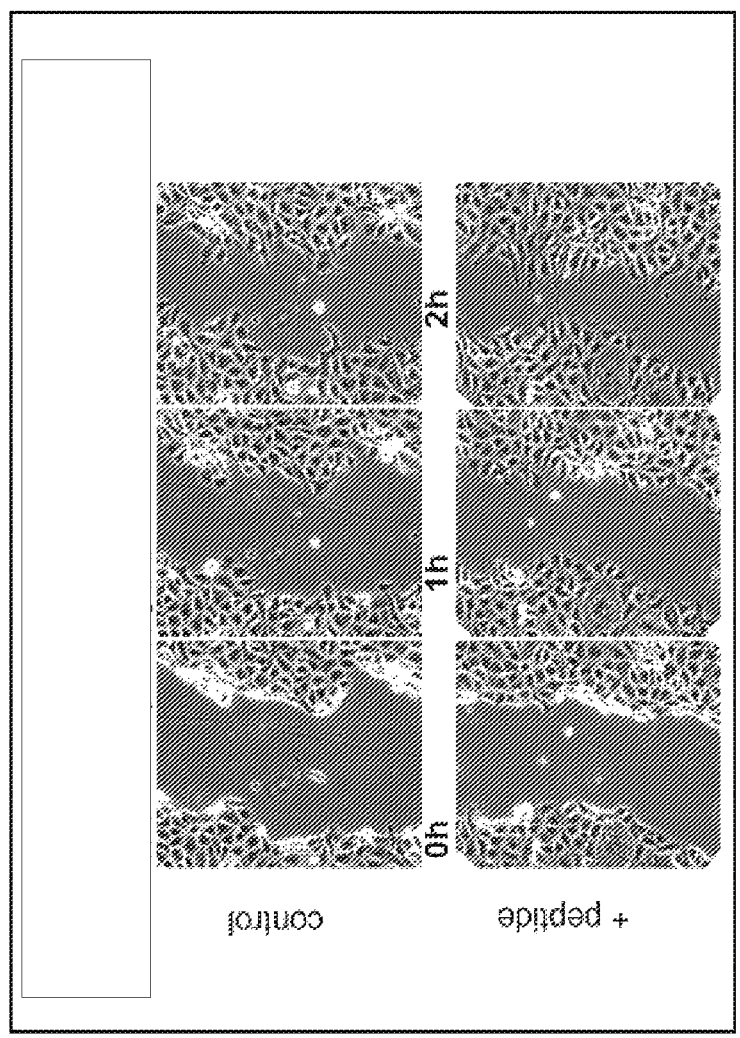
FIG. 1 shows a series of light microscope images depicting the results of a wound healing assay performed on capillary-derived vascular endothelial cells treated in the presence or absence of a wound healing peptide provided herein.

Other objects, features, and advantages of the technology provided herein will become apparent from the following detailed description. It should be understood, however, that the detailed description and the specific examples, while indicating preferred embodiments of the technology provided herein, are given by way of illustration only, since various changes and modifications within the spirit and scope of the technology provided herein will become apparent to those skilled in the art from this detailed description.

DETAILED DESCRIPTION OF THE INVENTION

Wound healing is predicated upon the migration and proliferation of cells at or near the wound edge and the recruitment of new or pre-existing blood vessels to the wound site. Provided herein are wound healing peptides (WHPs) that stimulate keratinocyte and/or endothelial cell motility and/or proliferation. Also provided herein are kits and articles of manufacture comprising one or more of the WHPs.

Wound Healing Peptides (WHPs) and Encoding WHP Nucleic Acids

As described herein, treatment of purified collagens or extracellular matrices (ECM) with a bacterial collagenase, such as collagenase isolated from a Clostridial bacterium results in the liberation of several previously unstudied oligopeptides. These peptides are generally not formed by the treatment of collagen or ECM with a human collagenase. These peptides can be isolated from digested collagen or ECM, or synthesized using conventional peptide synthesis methods well-known in the art. Further, combinatorial peptides can be generated by combining all or portions of two or more WHPs. Exemplary peptides are provided in Table 1.

TABLE 1

| SEQ ID NO: | Amino Acid Sequence | SEQ ID NO: | Nucleic Acid Sequence |
|---|---|---|---|
| 1 | DINECEIGAPAGE | 14 | 5'-GAYATHAAYGARTGYGARATHGGNGCNCCNGCNGGNGAR |
| 2 | DINECEIGAPAGEETEVTVEG | 15 | 5'-GAYATHAAYGARTGYGARATHGGNGCNCCNGCNGGNGARGARACNGARGTNACNGTNGARGGN |
| 3 | DINECEIGAPAGEETEVTVEGLEPG | 16 | 5'-GAYATHAAYGARTGYGARATHGGNGCNCCNGCNGGNGARGARACNGARGTNACNOTNGARGGNMTNGARCCNGGN |
| 4 | GEETEVTVEGLEPG | 17 | 5'-GGNGARGARACNGARGTNACNGTNGARGGNMTNGARCCNGGN |
| 5 | GVRSCPRGCSQKGRCED | 18 | 5'-GGNGTNMGNWSNTGYCCNMGNGGNTGYWSNCARAARGGNMGNTGYGARGAY |
| 6 | CVCWPGYTGRD | 19 | 5'-TGYGTNTGYTGGCCNGGNTAYACNGGNMGNGAY |
| 7 | CGTRACPGDC | 20 | 5'-TGYGGNACNMGNGCNTGYCCNGGNGAYTGY |
| 8 | CVCPPGYTGP | 21 | 5'-TGYGTNTGYCCNCCNGGNTAYACNGGNCCN |
| 9 | DINECELSANL | 22 | 5'-GAYATHAAYGARTGYGARMTNWSNGCNAAYMTN |
| 10 | DIDECESSPCINGV | 23 | 5'-GAYATHGAYGARTGYGARWSNWSNCCNTGYATHAAYGGNGTN |

TABLE 1-continued

| SEQ ID NO: Amino Acid Sequence | SEQ ID NO: Nucleic Acid Sequence |
|---|---|
| 11 MFRKPIPSTVKA | 24 5'-ATGTTYMGNAARCCNATHCCNWSNACNGTNAARGCN |
| 12 IISRCQVCMKMRP | 25 5'-ATHATHWSNMGNTGYCARGTNTGYATGAARATGMGNCCN |
| 13 MFRKPIPSTVKAPPIISR CQVCMKMRP | 26 5'-ATGTTYMGNAARCCNATIICCNWSNACNGTNAARGCNCCN CCNATHATHWSNMGNTGYCARGTNTGYATGAARATGMGN CCN |

The methods, kits, and articles of manufacture provided herein can include more than one peptide, wherein at least one of the peptides is selected from SEQ ID NO. 1-3. The methods, kits, and articles of manufacture provided herein can include more than one peptide, wherein at least one of the peptides is selected from SEQ ID NO. 4-13. The methods, kits, and articles of manufacture provided herein can include one or more polypeptides that comprise one or more of SEQ ID NO. 1-3 or one or more of SEQ ID NO. 4-14. In some embodiments, the peptides can be linked consecutively.

The wound-healing properties of WHPs have been demonstrated in vitro, using well characterized methods and wound healing assays, including certain assays developed in the inventor's laboratory. The results of these in vitro assays are described herein. It is recognized that some of the WHPs disclosed herein do not stimulate the epithelial (e.g., keratinocyte) wound healing responses, but do promote the angiogenesis of wound healing, as demonstrated by enhanced capillary endothelial cell migration, proliferation and morphogenesis.

Referring to FIG. 1, an in vitro wound healing assay was performed in the presence or absence of a WHP (SEQ ID NO: 9) to demonstrate that the WHP promotes and potentiates the migration of capillary endothelial cells. In this assay, capillary endothelial cells were plated on tissue culture plastic and allowed to form a confluent monolayer. The monolayer was mechanically disrupted and non-adherent cells were removed, at which point the WHP was provided at a concentration within the range of sub-nanomolar (0.5 nM) to sub-millimolar (0.2 mM) in tissue culture media (DMEM with 1% bovine calf serum. Control cultures were incubated with serum alone, positive control test substances, e.g. basic fibroblast growth factor (bFGF viz, FGF2) and vascular endothelial growth factor (VEGF) (for capillary-derived endothelial cells); or heparin-binding epidermal-like growth factor (HbEGF) (for human skin derived keratinocytes). Other control cultures were incubated with either no peptide or a random peptide without wound healing or proliferative properties. The extent of endothelial cell migration in the WHP and control cultures was observationally determined at various time points following injury (e.g., thirty minutes, one hour, two hours, or more than two hours). As shown in FIG. 1, after both one and two hours post-injury, endothelial cells treated with a WHP have substantially greater migration into the wound site.

Figure 2:
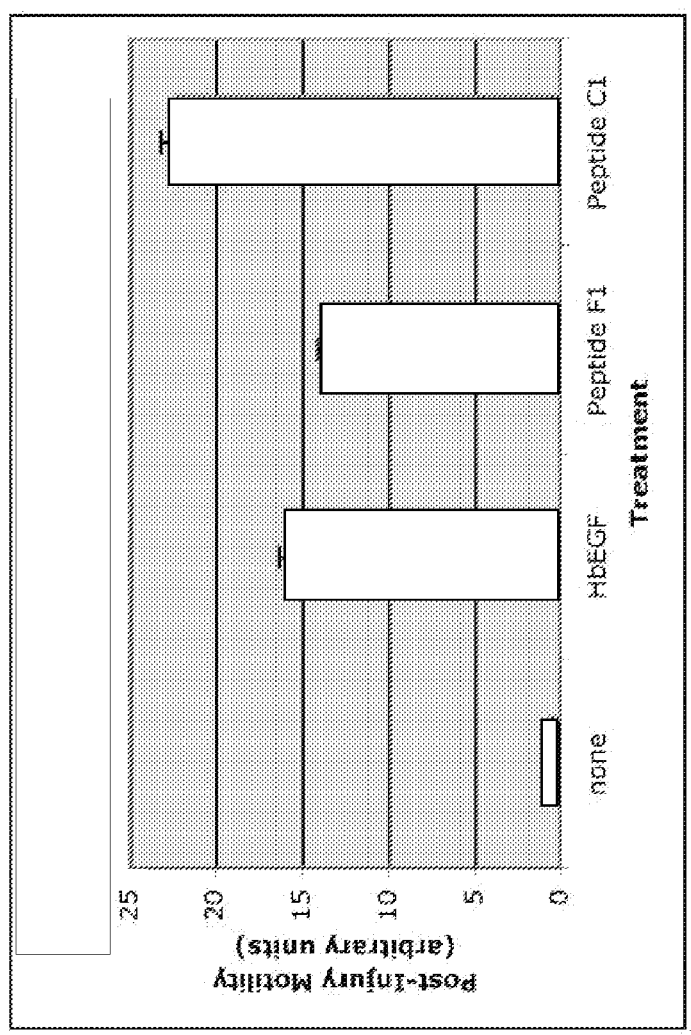
FIG. 2 is a bar graph showing an increase in motility of human epidermal-derived keratinocytes using two different wound healing peptides, SEQ ID NO: 3 and SEQ ID NO: 9, provided herein.

Referring to FIG. 2, an in vitro wound healing assay was performed to compare the wound healing properties of two WHPs, SEQ ID NO: 3 and SEQ ID NO: 9, with a known potentiator of keratinocyte migration, heparin-binding EGF-like growth factor (HbEGF). In these experiments, confluent densities of human epidermal-derived keratinocytes were plated in vitro in defined media lacking WHPs or positive control substances. At time zero, all cultures are wounded mechanically and imaging of wounds was accomplished automatically using computer-assisted light microscope imaging. Cell cultures were injured mechanically by removing defined zones of living cells were then washed and test agents or control substances delivered. Cells recovering from injury were than quantifiably monitored using computer-assisted imaging and light microscopy. Post-injury motility was assessed using the migratory response of untreated injured cultures as a baseline for quantitative comparative analysis. Multiple experiments with multiple replicates are shown, standard deviation with error of the mean. Keratinocyte post-injury motility was measured to and displayed in FIG. 2 in arbitrary units. As compared to a growth factor known to be migration-inducing in keratinocytes, both tested WHPs were equal or superior to the growth factor.

Figure 3:
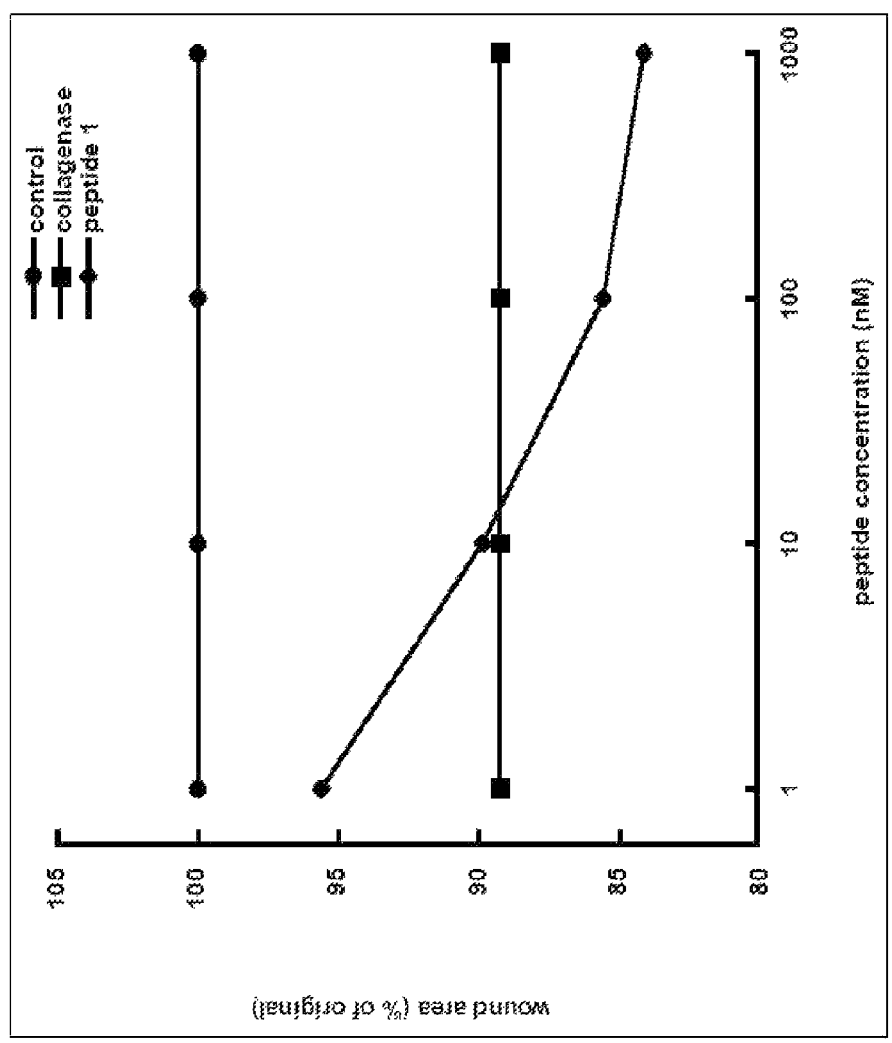
FIG. 3 is a line graph showing the dose-dependent wound healing activity of a wound healing peptide, SEQ ID NO: 9, provided herein.

Referring to FIG. 3, the WHPs provided herein act in dose-dependent manner. A WHP, SEQ ID NO: 9, was provided in an in vitro injury model at concentrations ranging from 1 to 1000 nM.

Figure 4:
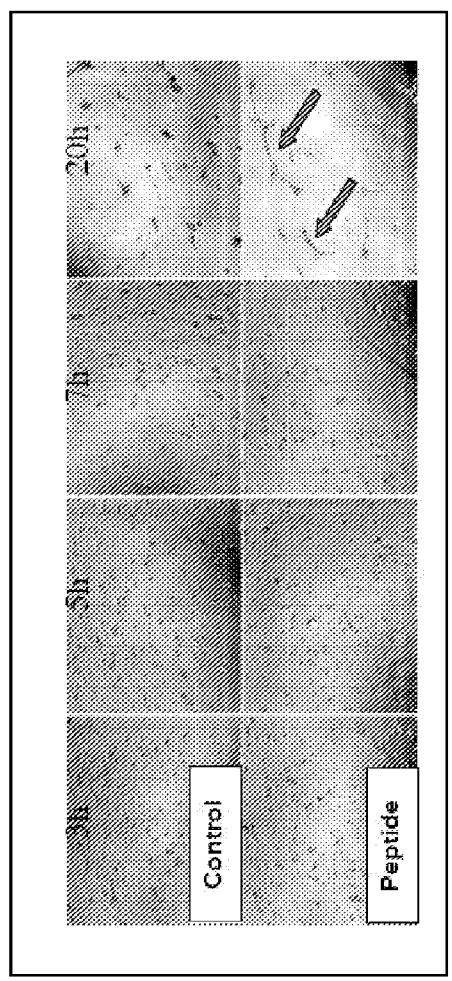
FIG. 4 contains a series of photomicrographic images depicting the results of an in vitro angiogenesis assay performed in the presence or absence of a wound healing peptide, SEQ ID NO: 9, provided herein.

The WHPs provided herein are also useful in the promotion of capillary morphogenesis. An in vitro capillary morphogenesis assay was performed to demonstrate that WHPs induce formation of capillary tube like structures when contacted with endothelial cells. Specifically, isolated capillary endothelial cells were embedded in an ECM-derived three-dimensional matrix that contained a WHP at a range of concentrations from the nanomolar (nM) to sub-millimolar (mM) (e.g., between 0.5 nM-0.2 mM) and incubated. As demonstrated in FIG. 4, endothelial cells contacted with a WHP and incubated for a period of twenty hours formed multicellular tubules within the ECM matrix. In comparison, negative control cell populations (i.e., cells that were not exposed to a WHP but were exposed to serum containing media, which contains growth factors and other angiogenesis inducers) generally remained as individual cells during this timeframe at this population density. Positive control cell populations (cells exposed to growth factors such as bFGF (also known as FGF2)) demonstrated that bFGF was able to promote in vitro angiogenesis to a lesser extent than populations treated with a WHP.

Figure 5:
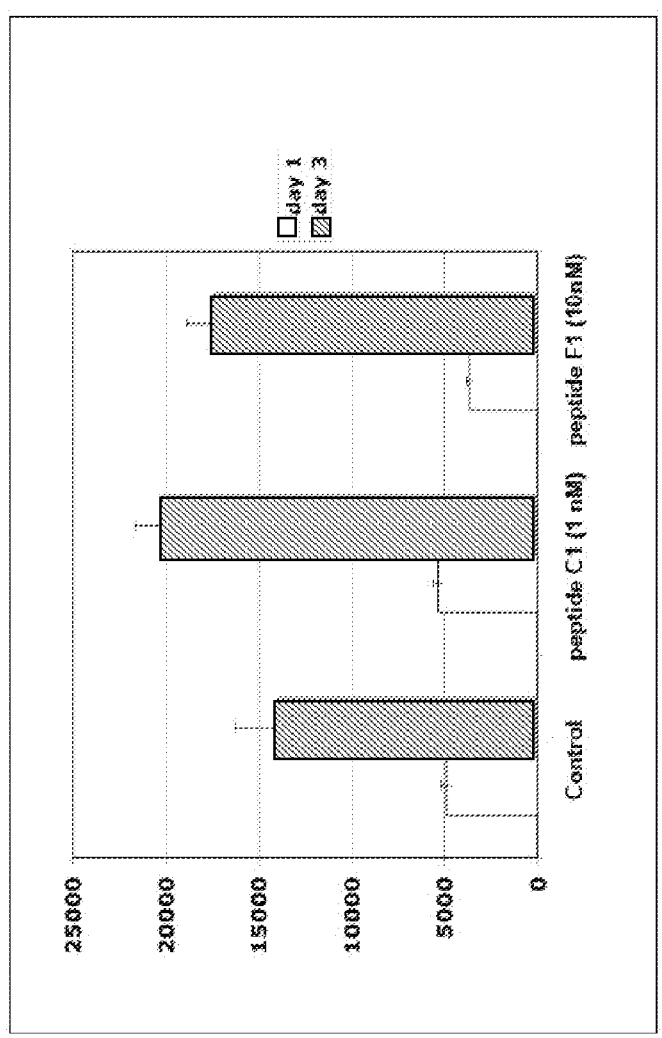
FIG. 5 is a bar graph showing an increase in endothelial cell proliferation in the presence of two wound healing peptides, SEQ ID NO: 3 and SEQ ID NO: 9, provided herein.

The WHPs provided herein induce endothelial cell proliferation. FIG. 5 is a bar graph that shows an increase in endothelial cell proliferation in the presence of a wound healing peptide (SEQ ID NO: 3 or SEQ ID NO: 9) provided at a concentration of 1 nM. Endothelial cells were plated at sub-confluent concentrations and allowed to attach, then new culture media was provided in the presence or absence of a WHP; control cultures were grown in 5% BCS DMEM.

Figure 6:
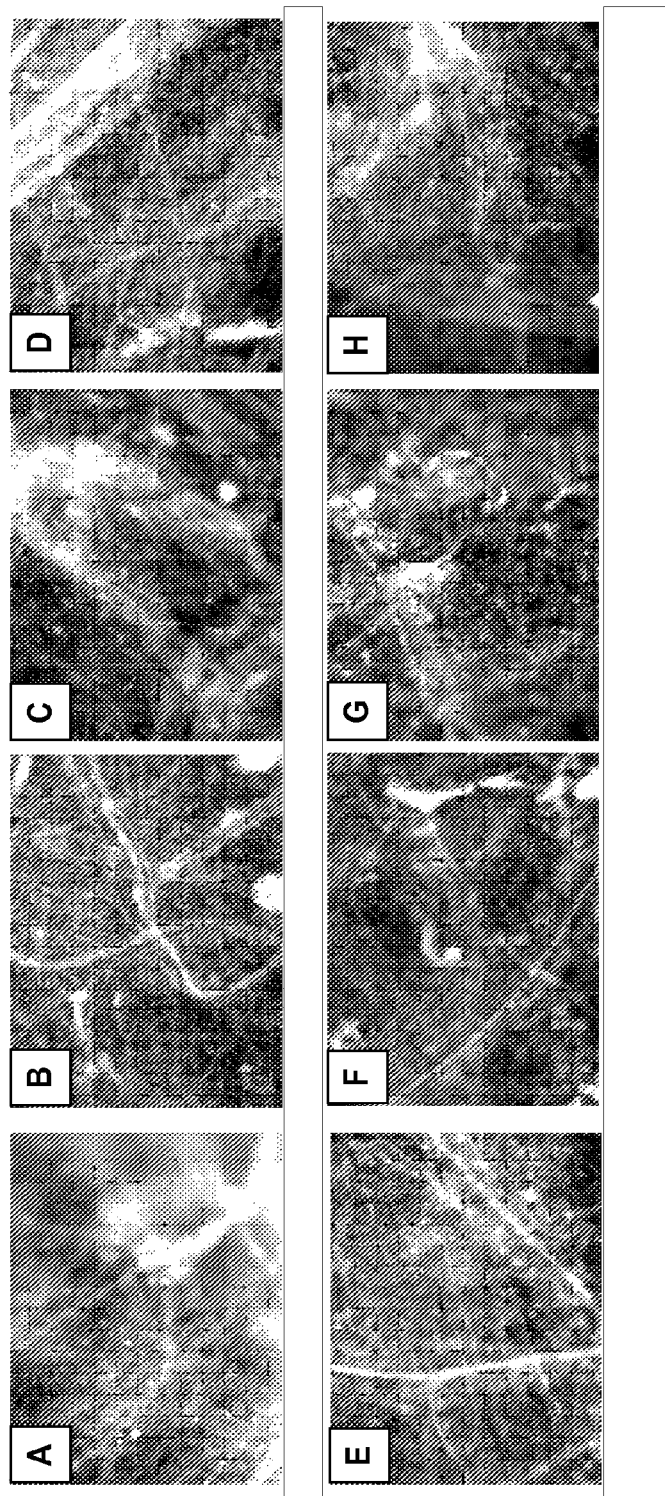
FIG. 6 contains a series of photographic images (A-H) depicting the results of an in vitro assay wherein a commercially available wound healing scaffold, Oasis®, has been functionalized with Ten4 peptide (SEQ ID NO:7), which has enabled the attachment and proliferation of capillary-derived vascular endothelial cells (appearing in red-orange (speckled white spots), vitally stained as described). In comparison to control scaffold, lacking the addition/functionalization with the Ten4 peptide (SEQ ID NO:7), the number and abundance of the capillary-derived endothelial cells present within the scaffold material that has been functionalized with Ten4 peptide (SEQ ID NO:7) (as visualized using vital fluorescence microscopy (filamentous and/or hazy white)) is significantly enhanced.

The WHPs provided herein were also used in conjunction with a bio-compatible wound product. As described herein, the wound product can be, for example, a biomaterial derived from mammalian tissue. The wound product can be provided in purified or unpurified form. In addition, the wound product can be modified by the addition of one or more compounds that act as functional crosslinkers (e.g., 1-Ethyl-3-[3-dimethylaminopropyl]carbodiimide hydrochloride (EDC) or N-hydroxysulfosuccinimide (sulfo-NHS)). Referring to FIG. 6, a commercially-available wound product (OASIS® Wound Matrix, Healthpoint Ltd., Fort Worth, Tex.) was combined with a WHP, in the presence or absence of one or more functional crosslinkers, and upon which were placed a suspension of capillary endothelial cells (for example, 100,000 cells per 1.0 by 0.5 cm section of wound product). Image analysis was performed using confocal microscopy.

Specifically, FIG. 6A shows control capillary-derived vascular endothelial cells (appearing in red-orange (speckled white spots), vitally stained as described) in the presence of Oasis® matrix alone. In FIGS. 6B, 6C, and 6D the cells were treated with crosslinker, 0.02 mM Ten4 peptide, and 0.2 mM Ten4 peptide (SEQ ID NO:7), respectively. FIGS. 6E and 6F show resulting cells after sequential addition of the crosslinker and the Ten4 peptide, with 0.02 mM Ten4 peptide in FIG. 6E and 0.2 mM Ten4 peptide (SEQ ID NO:7) in FIG. 6F. FIGS. 6G and 6H show resulting cells after simultaneous addition of the crosslinker and the Ten4 peptide (SEQ ID NO:7), with 0.02 mM Ten4 peptide (SEQ ID NO:7) in FIG. 6G and 0.2 mM Ten4 peptide (SEQ ID NO:7) in FIG. 6H. The Ten4 peptide (SEQ ID NO:7) enabled the attachment and proliferation of capillary-derived vascular endothelial cells. In comparison to control (FIGS. 6A and 6B), lacking the addition/functionalization with the Ten4 peptide, the number and abundance of the capillary-derived endothelial cells present within the matrix material that has been functionalized with Ten4 peptide (SEQ ID NO:7) is significantly enhanced.

WHPs in Combination Treatment with Other Wound Healing Materials

Provided herein are methods for the treatment of wounds using WHPs in combination with other biological materials that promote or augment wound healing responses. Such biological materials include, without being limited to, growth factors, cytokines, enzymes, and ECM components. For example, collagenase treatment of the sub-endothelial extracellular matrix in combination with WHP treatment synergistically accelerates endothelial migration and proliferation to a level greater than the inductive influence of collagenase treatment in the absence of WHPs.

Kits, Articles of Manufacture, and Absorbent Products

Provided herein are kits for the treatment of wounds in a subject, containing a WHP. In some embodiments, the kit includes instructions for using the peptide to treat a wound or wounds in the subject. In some embodiments, the kit includes one or more other materials that enhance wound healing. For example, the kit can contain a bio-compatible wound product, a growth factor, a cytokine, or an enzyme. Suitable subject, include, for example, a patient with having a wound. In some embodiments, the patient has diabetes. In other embodiments, the subject can be a burn patient. In some embodiments, the wound is a chronic wound. A non-human (e.g., bacterial) collagenase may also be included in the kit.

Articles of manufacture are also provided. For example, an article of manufacture includes a WHP (e.g., a peptide containing SEQ ID NOs: 1-3) and a growth factor, cytokine, or enzyme. The article is suitable for use in a medical treatment of a mammalian subject. For example, the article can be or include a skin or tissue equivalent. In some embodiments, the article comprises a growth factor, cytokine, or enzyme. A non-human (e.g., bacterial) collagenase may also be included in or on the article.

Provided herein are absorbent products. Suitable absorbent products, for example, are capable of absorbing a wound fluid when applied at a wound site. In some embodiments, the absorbent product comprises a structure that is capable of absorbing liquid and a WHP. Exemplary structures include, for example, bandages, gauzes, wound or sore dressings, dermal patches and adhesive tapes. The term "liquid absorbent structure" refers broadly to any material applied to a wound for protection, absorbance, drainage, etc. Thus, adsorbent and absorbent materials are specifically contemplated as a solid support. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer). Specifically contemplated is the use of liquid absorbent structures where the WHP is impregnated within or attached (covalently or otherwise) to the surface of the structure.

Anti-WHP Antibodies

Antibodies or antibody fragments which are directed against an WHP, which can be used in accordance with the technology provided herein are also provided. The term "antibody" means one or more antibodies. Included in the term antibodies are immunoglobulins, whether natural or partially or wholly produced artificially, e.g. recombinant. An antibody may be monoclonal or polyclonal. The antibody may, in some cases, be a member of one, or a combination immunoglobulin classes, including: IgG, IgM, IgA, IgD, and IgE. Derivatives of the IgG class, however, are preferred, such as $IgG_1$ and $IgG_{2b}$ subclasses. The technology provided herein includes methods for making immunoglobulins, without regard to origin, cleavable by a protease resulting in $F(ab')_2$ fragments, where such immunoglobulins are otherwise not cleavable by pepsin or pepsin-like treatments to yield $F(ab')_2$ fragments. The term "antibody fragment" refers to one or more derivatives of an antibody that is less than full-length. Preferably, the antibody fragment retains at least a significant portion of the full-length antibody's specific antigen binding ability. Examples of antibody fragments include, but are not limited to Fabs, $F(ab')_2$s, and scFvs. An "$F(ab')_2$" fragment is an antibody fragment, for example, one essentially equivalent to that obtained from certain pepsin cleavable immuno globulins (typically IgG) by digestion with pepsin at about pH 4.0-4.5. See, Parham, P. (1986). Preparation and purification of active fragments from mouse monoclonal antibodies. In Handbook of Experimental Immunology, Vol. 1: Immunochemistry (D. M. Wier, ed.) pp14.1-14.23. Blackwell Scientific, Oxford.

WHP Synthesis, Expression and Purification

WHPs described herein can be produced synthetically, or by proteolytic digestion of suitable biological materials by one or more enzymes such as collagenase. Alternatively, nucleotide sequences encoding WHPs can be introduced into a protein expression vector and produced in a suitable host organism (e.g., bacteria, insect cells, etc), then purified. Certain WHPs are combinatorially derived peptides (i.e., these peptides are not naturally occurring and cannot be produced by in situ cleavage). Instead, combinatorial peptides are produced by chemical synthesis. Non-limiting examples of combinatorial peptides include peptides that comprise one or more of SEQ ID NOs 1-3.

Modified WHPs

The WHPs provided herein can be modified by means well-known in the art. For example, the WHPs are modified by the addition of one or more functional groups such as phosphate, acetate, or various lipids and carbohydrates. WHPs can also exist as peptide derivatives. The term "peptide derivative" refers to compound having an imino group (—NH—), and more particularly, a peptide bond. Peptides may be regarded as substituted amides. Like the amide group, the peptide bond shows a high degree of resonance stabilization. The C—N single bond in the peptide linkage has typically about 40 percent double-bond character and the C═O double bond about 40 percent single-bond character. "Protecting groups" are those groups that prevent undesirable reactions (such as proteolysis) involving unprotected functional groups. In one embodiment, the protecting group is an acyl or an amide. In one embodiment, the acyl is acetate. In another embodiment, the protecting group is a benzyl group. In another embodiment, the protecting group is a benzoyl group. The technology provided herein includes combinations of such protecting groups.

"Peptide" or "polypeptide" refers to a polymer in which the monomers are alpha amino acids joined together through amide bonds. Peptides are two or often more amino acid monomers long. The term "dimer" as in a peptide "dimer" refers to a compound in which two peptide chains are linked; generally, although not necessarily, the two peptide chains will be identical and are linked through a linking moiety covalently bound to the carboxyl terminus of each chain. Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gin or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. Stereoisomers (e.g., D-amino acids) of the twenty conventional amino acids, unnatural amino acids such as $\alpha$, $\alpha$-disubstituted amino acids, N-alkyl amino acids, lactic acid, and other unconventional amino acids may also be suitable components for compounds of the technology provided herein. Examples of unconventional amino acids include: $\beta$-alanine, 1-naphthylalanine, 2-naphthylalanine, 3-pyridylalanine, 4-hydroxyproline, O-phosphoserine, N-acetylserine, N-formylmethionine, 3-methylhistidine, 5-hydroxylysine, nor-leucine, and other similar amino acids and imino acids (e.g., 4-hydroxyproline).

An additional polypeptide ("tag") can be added on for the purpose of purifying or identifying or purifying the WHPs. Protein tags make it possible, for example, for the polypeptides to be adsorbed, with high affinity, to a matrix, and for the matrix then to be washed stringently with suitable buffers without the complex being eluted to any significant extent, and for the adsorbed complex subsequently to be eluted selectively. Examples of the protein tags which are known to the skilled person are a (His)6 tag, a Myc tag, a FLAG tag, a haemagglutinin tag, a glutathione transferase (GST) tag, intein having an affinity chitin-binding tag or maltose-binding protein (MBP) tag. These protein tags can be located N-terminally, C-terminally and/or internally.

"Pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium and protamine zinc salts, which are prepared by methods well known in the art. The term also includes non-toxic acid addition salts, which are generally prepared by reacting the compounds provided herein with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate and the like. "Pharmaceutically or therapeutically effective dose or amount" refers to a dosage level sufficient to induce a desired biological result. That result can be alleviation of the signs, symptoms, or causes of a disease, or any other desired alteration of a biological system. Preferably, this dose or amount will be sufficient to stimulate or augment the epithelial and/or endothelial wound healing response and, thus, induce or potentiate wound healing.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

The WHPs are administered orally, topically, or by parenteral means, including subcutaneous and intramuscular injection, implantation of sustained release depots, intravenous injection, intranasal administration, and the like. Accordingly, WHPs may be administered as a pharmaceutical composition comprising a WHP in combination with a pharmaceutically acceptable carrier or excipient. Such compositions may be aqueous solutions, emulsions, creams, ointments, suspensions, gels, liposomal suspensions, and the like. Suitable carriers (excipients) include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene®, Aquaphor®, and the like. Other topical formulations include aerosols, bandages and other wound dressings. Alternatively one may incorporate or encapsulate the WHP in a suitable polymer matrix or membrane, thus providing a sustained-release delivery device suitable for implantation near the site to be treated locally. Other suitable devices for delivering or administering the compositions provided herein include indwelling catheters and devices such as the Alzet® minipump. Ophthalmic preparations may be formulated using commercially available vehicles such as Sorbi-care®, Neodecadron®, Lacrilube®, and the like or may employ topical preparations such as that described in U.S. Pat. No. 5,124,155, incorporated herein by reference. Further, one may provide a VEGF antagonist in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

The technology provided herein is not limited to the particular methodologies, protocols, constructs, formulae and reagents described but further include those known to the skilled artisan. It is also to be understood that the terminology used herein is for the purpose of describing particular embodiments only, and is not intended to limit the scope of the technology provided herein.

Unless defined otherwise, all technical and scientific terms used herein have the same meaning as commonly understood to one of ordinary skill in the art to which technology provided herein belongs. Any methods, materials, and kits similar or equivalent to those described herein can be used in the practice or testing of the technology provided herein.

What is claimed is:

1. A method to promote wound healing in a subject in need thereof, comprising administering to the subject a peptide consisting essentially of an amino acid sequence selected from the group consisting of SEQ ID Nos: 4-10 and 13.

2. The method of claim 1, wherein the peptide is administered in an amount effective to enhance the rate of migration of keratinocytes or endothelial cells, or a combination of keratinocytes and endothelial cells, towards a wound edge.

3. The method of claim 1, wherein the administration of the peptide results in an increase in the re-epithelialization of the wound.

4. The method of claim 1, wherein the administration of the peptide results in an increase in angiogenesis in or near the wound.

5. The method of claim 1, wherein the peptide is administered at a wound site.

6. The method of claim 1, wherein the wound is a thermal, chronic, acute or surgical wound.

7. The method of claim 1, further comprising administering to the subject a second agent.

8. The method of claim 7, wherein the second agent is a polypeptide.

9. The method of claim 7, wherein the second agent is a growth factor, cytokine, or enzyme.

10. The method of claim 7, wherein the second agent is a non-human collagenase.

11. The method of claim 10, wherein the non-human collagenase is bacterial collagenase.

12. The method of claim 1, wherein the subject is a mammalian subject.

13. The method of claim 12, wherein the mammalian subject is a human.

* * * * *